US006468519B1

(12) United States Patent
Uhrich

(10) Patent No.: US 6,468,519 B1
(45) Date of Patent: Oct. 22, 2002

(54) POLYANHYDRIDES WITH BIOLOGICALLY ACTIVE DEGRADATION PRODUCTS

(75) Inventor: Kathryn Elizabeth Uhrich, Hoboken, NJ (US)

(73) Assignee: Rutgers, The State University of New Jersey, New Burnswick, NJ (US)

( * ) Notice: Subject to any disclaimer, the term of this patent is extended or adjusted under 35 U.S.C. 154(b) by 0 days.

(21) Appl. No.: 09/422,294

(22) Filed: Oct. 21, 1999

Related U.S. Application Data

(63) Continuation-in-part of application No. PCT/US98/18816, filed on Sep. 10, 1998.
(60) Provisional application No. 60/058,328, filed on Sep. 10, 1997.

(51) Int. Cl.[7] .................. A61K 31/74; A61K 31/77; A61K 31/765
(52) U.S. Cl. .................. 424/78.01; 424/78.19; 424/78.17; 424/78.37
(58) Field of Search .................. 424/78.01, 78.19, 424/78.17, 78.37; 514/17, 21; 528/206

(56) References Cited

U.S. PATENT DOCUMENTS

| | | | |
|---|---|---|---|
| 4,062,855 A | 12/1977 | Allan et al. | 260/295 PA |
| 4,126,445 A | 11/1978 | Allan et al. | 71/94 |
| 4,612,302 A | 9/1986 | Szabo et al. | 514/11 |
| 4,684,620 A | 8/1987 | Hruby et al. | 514/11 |
| 4,757,128 A | 7/1988 | Domb et al. | 528/271 |
| 4,792,598 A | 12/1988 | Ziegast | 528/206 |
| 4,857,311 A | 8/1989 | Domb et al. | 424/78 |
| 4,868,274 A | 9/1989 | Gupta et al. | 528/206 |
| 4,886,870 A | * 12/1989 | D'Amore et al. | 528/206 |
| 4,888,176 A | 12/1989 | Langer et al. | 424/426 |
| 4,891,225 A | 1/1990 | Langer et al. | 424/428 |
| 4,906,474 A | 3/1990 | Langer et al. | 424/428 |
| 4,938,949 A | 7/1990 | Borch et al. | 424/10 |
| 4,997,904 A | 3/1991 | Domb | 528/206 |
| 4,999,417 A | 3/1991 | Domb | 528/271 |
| 5,082,925 A | 1/1992 | Shalaby et al. | 528/354 |
| 5,175,235 A | 12/1992 | Domb et al. | 528/271 |
| 5,259,968 A | 11/1993 | Emert et al. | 252/51.5 A |
| 5,264,540 A | 11/1993 | Cooper et al. | 528/272 |
| 5,498,729 A | 3/1996 | Domb | 548/500 |
| 5,514,764 A | 5/1996 | Fretchet et al. | 528/10 |
| 5,545,409 A | 8/1996 | Laurencin et al. | 424/426 |
| 5,629,009 A | 5/1997 | Laurencin et al. | 424/426 |
| 5,837,278 A | 11/1998 | Geistlich et al. | 424/444 |
| 5,902,110 A | 5/1999 | Alfano et al. | 433/215 |
| 5,902,599 A | 5/1999 | Anseth et al. | 424/426 |
| 5,942,252 A | 8/1999 | Tice et al. | 424/501 |
| 6,071,530 A | 6/2000 | Polson et al. | 424/426 |

FOREIGN PATENT DOCUMENTS

| | | | |
|---|---|---|---|
| DE | 288311 | 3/1991 | A01N/25/10 |
| DE | 288387 | 3/1991 | C08G/67/04 |
| EP | 0246341 | 11/1987 | A61L/27/00 |
| NL | 9000237 | 8/1991 | A61K/31/60 |
| WO | WO-90/09779 | 9/1990 | A61K/7/16 |
| WO | WO-91/09831 | 7/1991 | C07C/69/035 |
| WO | 97/39738 | 10/1997 | A61K/9/16 |
| WO | 98/36013 | 8/1998 | C08G/64/00 |
| WO | 99/12990 | 3/1999 | C08G/63/00 |
| WO | 99/29885 | 6/1999 | C12P/1/00 |

OTHER PUBLICATIONS

Conix, A., "Aromatic Polyanhydrides, a New Class of High Melting Fiber–Forming Polymers", *Journal of Polymer Science, XXIX*, pp. 343–353, (1958).

Conix, A., "New High–Melting Fibre–Forming Polymers", *Die Makromolekulare Chemie, XXIV*, pp. 76–78, (1957).

Conix, A., "Poly[1, 3–bis(p–carboxyphenoxy)—Propane anhydride]", *Macromolecular Synthesis, 2*, pp. 95–99, (1996).

Erdman, L., et al., "Polymer Prodrugs with Pharmaceutically Active Degradation Products", *Polymer Preprints, 38* (2), pp. 570–571, (1997).

Gouin, S., et al., "New Polyanhydrides Made from a Bile Acid Dimer and Sebacic Acid: Synthesis, Characterization, and Degradation", *Macromolecules, 33*, pp. 5379–5383, (2000).

Jeffcoat, M.K., et al., "The Effect of Systemic Flurbiprofen on Bone Supporting Dental Implants", *Journal of American Dental Association, 126*, pp. 305–311, (Mar. 1995).

Langer, R., "New Methods of Drug Delivery", *Science, 249*, pp. 1527–1533, (Sep. 1990).

Macedo, B., et al., "The in vivo Response to a Bioactive Biodegadable Polymer", *Journal of Dental Research, 78*, Abstract No. 2827, p. 459, (1999).

March, J., *Advanced Organic Chemistry, Fourth Edition*, Jerry March, Ed., John Wiley & Sons, pp. 419–437, (1992).

Yazdi, M., et al., "Effects of non–steroidal anti–inflammatory drugs on demineralized bone–induced bone formation", *Journal of Periodontal Research, 27 (1)*, pp. 28–33, (Jan. 1992).

Anastasiou, T.J. ,et al. ,"Novel Polyanhydrides with Enhanced Thermal and Solubility Properties", *Macromolecules, 33 (17)*, (2000),pp. 6217–6221.

Anastasiou, T.J. ,et al. ,"Novel, Degradable Polyanhydrides", *25th Annual Meeting Transactions of the Society for Biomaterials*, Abstract,(1999),p. 79.

(List continued on next page.)

Primary Examiner—Thurman K. Page
Assistant Examiner—Blessing Fubara
(74) Attorney, Agent, or Firm—Schwegman, Lundberg, Woessner & Kluth P.A.

(57) ABSTRACT

Polyanhydrides which degrade into biologically active salicylates and alpha-hydroxy acids and methods of using these polyanhydrides to deliver the salicylates and alpha-hydroxy acids to a host are provided.

8 Claims, No Drawings

OTHER PUBLICATIONS

Anastasiou, T..J. ,et al. ,"Synthesis of Novel, Degradable Polyanhydrides Containing Para–Aminosalicyclic Acid as Drug Delivery Devices for Tuberculosis Treatment", *Polymer Preprints, 41* (2), (Aug. 2000),pp. 1366–1367.

Attawia, M..A. , et al. ,"Proliferation, Morphology, and Protein Expression by Osteoblasts Cultured on Poly(anhydride–co–amides)", *J. Biomed. Mater. Res. (Appl. Biomater), 48*, (1999),pp. 322–327.

Attawia, M.A. ,et al. ,"Regional drug delivery with radiation for the treatment of Ewing's sarcoma—In vitro development of a taxol release system", *Journal of Controlled Release, 71*, (2001),pp. 193–202.

Attawia, M..A. , et al. ,"The Long Term Osteoblast Reponse to Poly(anhydride–co–imides): A New Degradable Polymer for Use in Bone", *Proc. of the Fifth World Biomaterials Congress, Toronto, Canada*, (1996),p. 113.

Beaton, M..L. ,et al. ,"Synthesis of a novel poly(anhyidride–ester)", *The Rutgers Scholar—An Electronic Bulletin of Undergraduate Research, 3*, www.rutgersscholar.rutgers.edu/volume03/beatuhri/beatuhri.html,(2001), 7 pgs.

Bedell, C.,et al. ,"Processing and Hydrolytic Degradation of Aromatic, Ortho–Substituted Polyanhydrides", *Journal of Applied Polymer Science, 80*, (2001),pp. 32–38.

Campo, C..J. ,et al. ,"Polyanhydrides: the effects of ring substitution changes on polymer properties", *Polymer Bulletin, 42*, (1999),pp. 61–68.

Chafi, N..,"Dosage Form with Salicyclic Acid Attached to the Polyanhydride Polymer Dispersed in an Eudragit Matrix", *International Journal of Pharmaceutics, 52*, (1989),pp. 203–211.

Domb, A..J. ,"Synthesis and Characterization of Biodegradable Aromatic Anhydride Copolymers", *Macromolecules, 25*, (1992),pp. 12–17.

Dukovic, G.,et al. ,"Novel degradable poly(anhydride–esters) for controlled drug release", *The Rutgers Scholar—An Electronic Bulletin for Undgergraduate Research, 1*, http://rutgersscholar.rutgers.edu/colume01/uhriduko.html, (1991), 10 pgs.

Erdmann, L.., et al. ,"Chapter 5: Polymeric Prodrugs: Novel Polymers with Bioactive Components", In: *Tailored Polymeric Materials for Controlled Delivery Systems*, I. McCulloch, et al., (Editors), ACS Symposium Series 709, American Chemical Society: Washington, D.C.,(1998),pp. 83–91.

Erdmann, L.,et al. ,"Degradable poly(anhydride ester) implants: effects of localized salicyclic acid release on bone", *Biomaterials, 21*, (2000),pp. 2507–2512.

Erdmann, L..,et al. ,"Polymeric Prodrugs: Novel Polymers for Delivery of Salicyclic Acid", *Annals of Biomedical Engineering, 26 (Suppl. 1)*, Abstract No. PB.26, Annual Fall Meeting,(1988),p. S–124.

Erdmann, L..,"Polymeric Salicyclic Acid: In Vitro and In Vivo Degradation", *Polymer Preprints 39* (2), (1998), p. 224–225.

Erdmann, L..,et al. ,"Synthesis and Characterization of a Polymeric Prodrug", *Proceedings of the American Chemical Society Division of Polymeric Materials: Science and Engineering, 78*, Abstract of Spring Meeting, Dallas, TX,(1998), p. 194.

Erdmann, L..,et al. ,"Synthesis and degradation characteristics of salicyclic acid–derived poly(anhydrid–esters)", *Biomaterials, 21*, (2000),pp. 1941–1946.

Giammona, G..,"Polymeric Prodrugs alpha beta poly–hyroxyethyl–d1–aspartamide as macromolecular carrier for some non–steroidal anti–inflammatory agents", *Abstract from Database BIOSIS Online, Biosciences Information Service, Philadelphia, PA*, Original Publication from the International Journal of Pharmaceutics (Amsterdam), (1989), 1 pg.

Krogh–Jespersen, E.,et al. ,"Synthesis of a Novel Aromatic Polyanhydride Containing Aminosalicyclic Acid", *Polymer Preprints, 41 (1)*, (2000),pp. 1048–1049.

Pinther, P..,"Synthesis of Polyanhydrides Containing Ester Groups", *Makromol. Chem., Rapid Commun., 11*, (1990),pp. 403–408.

Uhrich, K.E. ,et al. ,"In Vitro Degradation Characteristics of Poly(anhydride–imides) Containing Pyromellitylimidoalanine", *J. Appl. Polymer Sci., Part A., Polym. Chem., 34 (7)*, (1996),pp. 1261–1269.

Uhrich, K.E. ,et al. ,"In Vitro Degradation Characteristics of Poly(anhydride–imides) Containing trimellitylimidoglycine", *J. Appl. Polymer. Sci., 63 (11)*, (1997),pp. 1401–1411.

Uhrich, K.E. ,et al. ,"Poly(anhydride–ester) Degradation: Mechanical Changes and Correlation to Antibiotic Release", *American Chemical Society, Abstracts of Papers, Part 2, Abstract No. 121*, 2221st ACS National Meeting, San Diego, CA,(2001),1 pg.

Uhrich, K.E. ,et al. ,"Synthesis and Characterization of Degradable poly(anhydride–co–imides)", *Macromolecules, 28 (7)*, (1995),pp. 2184–2193.

Uhrich, K.E. ,et al. ,"Synthesis and Characterization of poly(anhydride–co–imides): Solution Polycondensation of Biodegradable Polymers Derived from Amino Acids", *Proc. of the American Chemical Society, Division of Polymeric Materials: Science and Engineering, 70*, Spring Meeting, San Diego, CA,(1994),pp. 239–240.

* cited by examiner

POLYANHYDRIDES WITH BIOLOGICALLY ACTIVE DEGRADATION PRODUCTS

This application is a continuation-in-part of PCT Application No. PCT/US98/18816, filed Sep. 10, 1998, which claims the benefit of provisional Application Ser. No. 60/058,328, filed Sep. 10, 1997.

FIELD OF THE INVENTION

Biocompatible polyanhydrides having improved degradation properties and processability with useful degradation products have now been developed. In one embodiment, the polyanhydrides are ortho-substituted aromatic polyanhydrides produced from ortho-substituted bis-aromatic carboxylic acid anhydrides which degrade into biologically active materials such as salicylates. In another embodiment, the polyanhydrides are aliphatic in structure and degrade into alpha-hydroxy acids. Salicylates are used routinely as anti-inflammatory, antipyretic, analgesic, and anti-oxidant agents, while alpha-hydroxy acids are incorporated into many skin moisturizers, cleansers, lotions, creams shampoos, tanning products and lipsticks to promote smoother, clearer skin with fewer wrinkles. Thus, the biocompatible polyanhydrides of the present invention can be administered to a host via a variety of routes including, but not limited to orally, subcutaneously, intramuscularly, intradermally and topically, depending upon the degradation product of the polyanhydride and the selected use for the degradation product.

BACKGROUND OF THE INVENTION

Polymers comprising aromatic or aliphatic anhydrides have been studied extensively over the years for a variety of uses. For example, in the 1930s fibers comprising aliphatic polyanhydrides were prepared for use in the textile industry. In the mid 1950s, aromatic polyanhydrides were prepared with improved film and fiber forming properties. More recently, attempts have been made to synthesize polyanhydrides with greater thermal and hydrolytic stability and sustained drug release properties.

U.S. Pat. Nos. 4,757,128 and 4,997,904 disclose the preparation of polyanhydrides with improved sustained drug release properties from pure, isolated prepolymers of diacids and acetic acid. However, these biocompatible and biodegradable aromatic polyanhydrides have radical or aliphatic bonds resulting in compounds with slow degradation times as well as relatively insoluble degradation products unless incorporated into a copolymer containing a more hydrophilic monomer, such as sebacic acid. The aromatic polyanhydrides disclosed in the '128 Patent and the '904 Patent are also insoluble in most organic solvents. A bioerodible controlled release device produced as a homogenous polymeric matrix from polyanhydrides with aliphatic bonds having weight average molecular weights greater than 20,000 and an intrinsic velocity greater than 0.3 dL/g and a biologically active substance is also described in U.S. Pat. No. 4,888,176. Another bioerodible matrix material for controlled delivery of bioactive compounds comprising polyanhydride polymers with a uniform distribution of aliphatic and aromatic residues is disclosed in U.S. Pat. No. 4,857,311.

Biocompatible and biodegradable aromatic polyanhydrides prepared from para-substituted bis-aromatic dicarboxylic acids for use in wound closure devices are disclosed in U.S. Pat. No. 5,264,540. However, these compounds exhibit high melt and glass transition temperatures and decreased solubility, thus making them difficult to process. The disclosed polyanhydrides also comprise radical or aliphatic bonds which can not be hydrolyzed by water.

Polyanhydride polymeric matrices have also been described for use in orthopedic and dental applications. For example, U.S. Pat. No. 4,886,870 discloses a bioerodible article useful for prosthesis and implantation which comprises a biocompatible, hydrophobic polyanhydride matrix. U.S. Pat. No. 5,902,599 also discloses biodegradable polymer networks for use in a variety of dental and orthopedic applications which are formed by polymerizing anhydride prepolymers.

Biocompatible and biodegradable polyanhydrides have now been developed with improved degradation, processing and solubility properties, as well as utilities based upon their degradation products.

SUMMARY OF THE INVENTION

An object of the present invention is to provide biocompatible and biodegradable polyanhydrides which degrade into biologically active products. In one embodiment, aromatic polyanhydrides which degrade into biologically active salicylates are prepared from ortho-substituted bis-aromatic carboxylic acid anhydrides. Ortho substitution disrupts the crystallinity of the resulting polymer, enhancing solubility and processability, as well as degradation properties. The use of hydrolyzable bonds such as esters, amides, urethanes, carbamates and carbonates as opposed to radical or aliphatic bonds in these compounds further enhances these properties. In this embodiment, the polyanhydride comprises a repeating unit within the structure of Formula I:

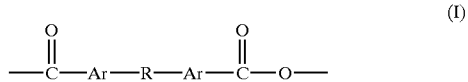

(I)

wherein Ar is a substituted or unsubstituted aromatic ring and R is a difunctional organic moiety substituted on each Ar ortho to the anhydride group. Ar and R are preferably selected so that the hydrolysis products of the polyanhydrides have a chemical structure resembling biologically active materials, particularly salicylates such as aspirin, non-steroidal anti-inflammatory naphthyl or phenyl propionates such as ibuprofen, ketoprofen, naproxen, and the like, or other aromatic anti-inflammatory compounds such as indomethacin, indoprofen, and the like. Ar is preferably a phenyl group and R is preferably $-Z_1-R_1-Z_1-$ in which $R_1$, is a difunctional moiety and both $Z_1$s are independently either an ester, amide, anhydride, carbonate, urethane or sulfide groups. $R_1$ is preferably an alkylene group containing from 1 to carbon atoms, or a group with 2–20 carbon atoms having a structure selected from $(-CH_2-CH_2-O-)_m$, $(CH_2-CH_2-CH_2-O-)_m$ and $(-CH_2-CHCH_3-O-)_m$.

Ortho-substituted bis-aromatic carboxylic acid anhydrides are used in the preparation of the aromatic polyanhydrides of the present invention. The ortho-substituted bis-aromatic carboxylic acid anhydrides have the structure of Formula II:

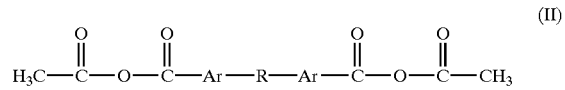

(II)

wherein Ar and R, and the preferred species thereof, are the same as described above with respect to Formula I and R is substituted on each Ar ortho to the anhydride group.

In another embodiment, polyanhydrides which degrade into biologically active alpha-hydroxy acids are prepared from bis-carboxylic acid anhydrides. In this embodiment, the polyanhydride comprises a repeating unit within the structure of Formula III:

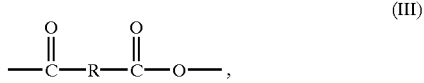
(III)

wherein, R is preferably selected so that the hydrolysis products of the polyanhydrides have a chemical structure resembling an alpha-hydroxy acid. In this embodiment, R is preferably an alkylene group containing from 1 to 20 carbon atoms, $-(CH_2)_x-$ wherein x is from 1 to 20, or

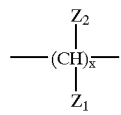

wherein x is from 1 to and $Z_1$ and $Z_2$ are OH so that the R group contains from 1 to 40 hydroxyl groups.

The present invention relates to compositions and methods of using compositions comprising polyanhydrides of Formula (I) or (III) in applications wherein delivery of a salicylate or an alpha-hydroxy acid to a host is desired. By "host" it is meant to include both animals and plants.

A more complete appreciation of the invention and other intended advantages can be readily obtained by reference to the following detailed description of the preferred embodiments and claims, which disclose the principles of the invention and the best modes which are presently contemplated for carrying them out.

DETAILED DESCRIPTION OF THE INVENTION

Polyanhydrides which degrade into useful biologically active products such as salicylates and alpha-hydroxy acids have now been developed. Compounds comprising these polyanhydrides are useful in a variety of applications wherein delivery of a salicylate or alpha-hydroxy acid is desired.

In one embodiment, the polyanhydride comprises repeating units with the structure of Formula I:

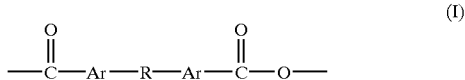
(I)

wherein Ar is a substituted or unsubstituted aromatic ring and R is a difunctional organic moiety substituted on each Ar ortho to the anhydride group. In this embodiment, Ar and R are preferably selected so that the hydrolysis products of the polyanhydrides have a chemical structure resembling biologically active materials, particularly salicylates such as aspirin, nonsteroidal anti-inflammatory naphthyl or phenyl propionates such as ibuprofen, ketoprofen, naproxen, and the like, or other aromatic anti-inflammatory compounds such as indomethacin, indoprofen, and the like. Examples of the biologically active salicylates include, but are not limited to, thymotic acid, 4,4-sulfinyldinailine, 4-sulfanilamidosalicylic acid, sulfanilic acid, sulfanilylbenzylamine, sulfaloxic acid, succisulfone, salicylsulfuric acid, salsallate, salicylic alcohol, orthocaine, mesalamine, gentisic acid, enfenamic acid, cresotic acid, aminosalicylic acid, aminophenylacetic acid, acetylsalicylic acid, and the like. The identification of Ar and R moieties that provide aromatic polyanhydrides that hydrolyze to form such biologically active salicylates can be readily determined by those of ordinary skill in the art without undue experimentation. In particular, Ar is preferably a phenyl group and R is preferably $-Z_1-R_1-Z_1-$ in which $R_1$, is a difunctional moiety and both $Z_1$s are independently either an ester, amide, anhydride, carbonate, urethane or sulfide groups. $R_1$ is preferably an alkylene group containing from 1 to carbon atoms, or a group with 2-carbon atoms having a structure selected from $(-CH_2-CH_2-O-)_m$, $(CH_2-CH_2-CH_2-O-)_m$ and $(-CH_2-CHCH_3-O-)_m$ or $R_1$ may have the structure $-R_2-Z_2-R_3-1$ wherein $R_2$ and $R_3$ are independently alkylene groups containing from 1 to 19 carbon atoms or groups having from 2 to 18 carbon atoms having a structure selected from $(-CH_2-CH_2-O-)_m$, $(-CH_2-CH_2-CH_2-O-)_m$, and $(-CH_2-CHCH_3-O-)_m$, and $Z_2$ is selected from the difunctional moieties described above with respect to $Z_1$.

Ar may be an alkylaryl group, in which a difunctional organic moiety is positioned between each anhydride carbonyl group and the corresponding aromatic ring. Preferably, however, each carbonyl group is directly substituted on the corresponding aromatic ring.

Preferred polymers of this embodiment have repeating units with the structure of Formula I in which Ar is a phenyl ring and R is selected from $-Z_1-(-CH_2-)_n-Z_1-$, $-Z_1(-CH_2-CH_2-O-)_m-Z_1-$, $-Z_1(-CH_2-CH_2-CH-O_2-)_m-Z_1-1$, and $-Z(-CH_2-CHCH_2-O-)_m-Z_1-$, wherein $Z_1$ is an ester or amide group and n is from 1 to inclusive, and preferably is 6, and m is selected so that R has from 2 to 20, and preferably 6, carbon atoms.

The aromatic polyanhydrides of this embodiment of the present invention may be prepared by the method described in Conix, Macromol. Synth., 2, 95–99 (1996), in which dicarboxylic acids are acetylated in an excess of acetic anhydride at reflux temperatures followed by melt condensation of the resulting carboxylic acid anhydride at 180° C. for 2–3 hours. The resulting polymers are isolated by precipitation into diethylether from methylene chloride. The described process is essentially the conventional method for polymerizing bisaromatic dicarboxylic acid anhydrides into aromatic polyanhydrides.

Aromatic polyanhydrides in accordance with this embodiment of the present invention have average molecular weights of at least about 1500 daltons, up to about 100,000 daltons, calculated by Gel Permeation Chromatography (GPC) relative to narrow molecular weight polystyrene standards.

These aromatic polyanhydrides are produced from ortho-substituted bis-aromatic carboxylic acid anhydrides having the structure of Formula II:

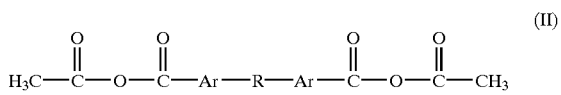
(II)

in which Ar, R and the preferred species thereof are the same as described above with respect to Formula I. As noted above, ortho-substituted bis-aromatic carboxylic acid anhydrides are prepared by acetylation of the corresponding ortho-substituted bis-aromatic carboxylic acids in an excess of acetic anhydride at ref lux temperatures. The dicarboxylic acids have the structure of Formula IV,

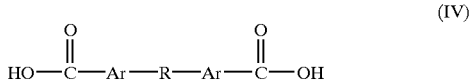

wherein Ar, R and the preferred species thereof are the same as described above with respect to Formula I.

The dicarboxylic acids are prepared by reacting a stoichiometric ratio of aromatic carboxylic acid having the structure $Z_3$—Ar—COOH and a compound having a structure $Z_4$—R—$Z_4$ wherein Ar is a substituted or unsubstituted aromatic ring on which $Z_3$ is substituted ortho to the carboxylic acid group, R is a difunctional organic moiety and $Z_3$ and $Z_4$ are functional groups selected to provide the linkage desired between the difunctional organic moiety and the two aromatic rings.

Suitable $Z_3$ and $Z_4$ functional groups, and the manner in which they may be reacted to produce the bis-aromatic dicarboxylic acids of the present invention, may be readily determined by those of ordinary skill in the art without undue experimentation. For example, for aromatic polyanhydrides having the structure of Formula I in which Ar is a phenyl group and R is —O—(CH$_2$—)$_6$—O—, the ortho-substituted bisaromatic dicarboxylic acid starting material may be prepared by reacting o-salicylic acid with 1,6-dibromohexane.

In another embodiment, the polyanhydrides degrade into biologically active alpha-hydroxy acids and comprise a repeating unit within the structure of Formula III:

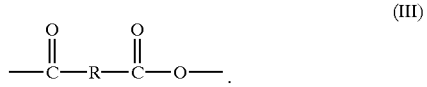

In this embodiment, R is preferably selected so that the hydrolysis products of the polyanhydrides have a chemical structure resembling an alpha-hydroxy acids. In this embodiment, R is preferably an alkylene group containing from 1 to 20 carbon atoms, —(CH$_2$)$_x$— wherein x is from 1 to 20, or

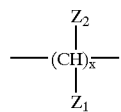

wherein x is from 1 to 20 and $Z_1$ and $Z_2$ are OH so that the R group contains from 1 to 40 hydroxyl groups. Examples of biologically active alpha-hydroxy acids include, but are not limited to, citric acid and malic acid. These polyanhydrides are prepared in the same fashion as described for aromatic polyanhydrides.

Polyanhydrides used in the present invention can be isolated by known methods commonly employed in the field of synthetic polymers to produce a variety of useful products with valuable physical and chemical properties. The new polymers can be readily processed into pastes or solvent cast to yield films, coatings, microspheres and fibers with different geometric shapes for design of various medical implants, and may also be processed by compression molding and extrusion. Medical implant applications include the use of aromatic polyanhydrides to form shaped articles such as vascular grafts and stents, bone plates, sutures, implantable sensors, implantable drug delivery devices, stents for tissue regeneration, and other articles that decompose harmlessly within a known time period. Polyanhydrides of the present invention can also be incorporated into oral formulations and into products such as skin moisturizers, cleansers, pads, lasters, lotions, creams, gels, ointments, solutions, shampoos, tanning products and lipsticks for topical application.

The quantity of aromatic polyanhydride that hydrolyzes to form an amount of biologically active salicylate or alpha-hydroxy acid effective for the selected use can be readily determined by those of ordinary skill in the art without undue experimentation. The quantity essentially corresponds stoichiometrically to the amount of salicylate or alpha-hydroxy acid known to produce an effective treatment for the selected use.

The present invention relates to methods of using compositions comprising these polyanhydrides in any application wherein delivery of a salicylate or alpha-hydroxy acid is desired. For example, salicylates such as salicylic acid are used routinely to treat many skin disorders including, but not limited to, acne, dandruff, psoriasis, seborrheic dermatitis of the skin and scalp, calluses, corns, common warts and plantar warts. Salicylic acid is also topically applied as an antiseptic for wounds, ulcers, and skin abscesses as it is known to exert powerful static effects against Gram-negative and Gram-positive bacteria, yeasts, dermatophytes, molds and other microbes. These antifungal properties also render salicylic acid useful in the treatment of athlete's foot. Accordingly, topical application of a composition comprising an aromatic polyanhydride of the present invention which degrades to a biologically active salicylate is expected to be useful in the treatment of all of these conditions and/or injuries.

The anti-bacterial activity of salicylic acid also renders these polyanhydrides useful in agricultural applications. Solutions comprising a polyanhydride of Formula (I) can be applied topically to plants to establish microbial resistance against a wide range of pathogens. Salicylic acid treatment has also been shown to induce thermotolerance in mustard seedlings. Accordingly, topical application of polyanhydrides of Formula (I) is also expected to induce thermotolerance in plants.

Salicylic acid has also been shown to have anti-cataract activity in patients suffering from galactosemic cataracts. Accordingly, a solution comprising an aromatic polyanhydride of Formula (I) can also be topically applied to the eye to inhibit cataract formation.

Salicylic acid is also a powerful anti-oxidant, neutralizing highly reactive, cell damaging molecules called free radicals. In fact, salicylic acid is often the standard by which the effectiveness of other anti-oxidants is measured. Anti-oxidants are administered orally and/or topically as antiviral agents. Anti-oxidants also inhibit UV-induced signal transduction and can be used as chemopreventative agents for skin cancer. In addition, the anti-oxidant properties of salicylates have been associated with anti-aging properties, protection against ischemia and reperfusion injury, and lowering of cholesterol levels and inhibition of clotting of blood. It is believed that compositions comprising an aromatic polyanhydride of Formula (I) will also exhibit these antioxidant properties. Thus, compositions comprising an aromatic polyanhydride of Formula (I) can also be used as antiviral agents, chemopreventative agents for skin cancer, anti-aging agents, and anti-clotting agents, and to provide protection against ischemia and reperfusion injury.

Compositions of the present invention comprising a polyanhydride of Formula (III) which degrades to an alpha-hydroxy acid can be incorporated into various topical formulations and applied to the skin to promote smoother, clearer skin with less wrinkles. It is generally accepted that regular use of alpha-hydroxy acids improves the appearance of the skin by minimizing fine lines, softening dry, rough skin patches and fading age spots. Alpha-hydroxy acids are effective exfoliators which dissolve the links that bind surface skin cells together causing dead cells to slough off. This process reveals the more youthful looking skin underneath which has more even skin tone, retains moisture and is less likely to form wrinkles. Topical application of a composition comprising a polyanhydride of Formula (III) provides an effective means for delivering alpha-hydroxy acids to the skin to promote smoother, clearer skin with less wrinkles.

The following non-limiting examples set forth hereinbelow illustrate certain aspects of the invention. All parts and percentages are by weight unless otherwise noted and all temperatures are in degrees Celsius. Except for acetic anhydride and ethyl ether (Fisher Scientific), all solvents and reagents were obtained from Aldrich Chemical. All solvents were HPLC grade. All other reagents were of analytical grade and were purified by distillation or recrystallization.

All compounds were characterized by a proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). Infrared spectroscopy was performed on an ATI Mattson Genesis (M100) FTIR Spectrophotometer. Samples were prepared by solvent casting on NaCl plates. $^1$H and $^{13}$C NMR spectroscopy was obtained on a Varian 200 MHZ or Varian 400 MHZ spectrometer in solutions of $CDCl_3$ or $DMSO-d_6$ with solvent as the internal reference.

GPC was performed on a Perkin-Elmer Advanced LC Sample Processor (ISS 200) with PE Series 200 LC Pump and a PE Series LC Refractive Index Detector to determine molecular weight and polydispersity. The data analysis was carried out using Turbochrom 4 software on a DEC Celebris 466 computer. Samples were dissolved in tetrahydrofuran and eluted through a mixed bed column (PE PL gel, 5 $\mu$m mixed bed) at a flow rate of 0.5 mL/minute. Samples (about 5 mg/mL) were dissolved into the tetrahydrofuran and filtered using 0.5 $\mu$m PTFE syringe filters prior to column injection. Molecular weights were determined relative to narrow molecular weight polystyrene standards (Polysciences, Inc.).

Thermal analysis was performed on a Perkin-Elmer system consisting of a TGA 7 thermal gravimetric analyzer equipped with PE AD-4 autobalance and Pyris 1 DSC analyzer. Pyris software was used to carry out data analysis on a DEC Venturis 5100 computer. For DSC, an average sample weight of 5–10 mg was heated at 10° C./minute at a psi flow of $N_2$. For TGA, an average sample weight of mg was heated at 20° C./minute under a 8 psi flow of $N_2$. Sessile drop contact angle measurements were obtained with an NRL Goniometer (Rame-hart) using distilled water. Solutions of polymer in methylene chloride (10% wt/volume) were spun-coated onto glass slips, at 5,000 rpm for seconds.

EXAMPLES

Example 1

Preparation of 1,6-Bis(o-Carboxyphenoxy) Hexane Dicarboxylic Acid

To a mixture of salicylic acid (77.12 g, 0.5580 mole) and distilled water (84 mL) sodium hydroxide (44.71 g, 1.120 mole) was added. The reaction was brought to reflux temperature before 1,6-dibromohexane (45.21 g, 0.2790 mole) was added drop-wise. Reflux was continued for 23 hours after which additional sodium hydroxide (11.17 g, 0.2790 mole) was added. The mixture was refluxed for 16 more hours, cooled, filtered, and washed with methanol. The yield was 48.8%.

Example 2

Preparation of 1,6-Bis(o-Carboxyphenoxy) Hexane Monomer (o-CPH)

The dicarboxylic acid of Example 1 was acetylated in an excess of acidic anhydride at reflux temperature. The resulting monomer was precipitated with methylene chloride into an excess of diethyl ether. The yield was 66.8%.

Example 3

Preparation of Poly(1,6-Bis(o-Carboxyphenoxy) Hexane) (Poly(o-CPH))

The monomer of Example 2 was polymerized in a melt condensation performed at 180° C. for 3 hours under vacuum in a reaction vessel with a side arm. The polymerization vessel was flushed with nitrogen at frequent intervals. The polymer was isolated by precipitation into diethyl ether from methylene chloride. The yield was quantitative.

All compounds were characterized by nuclear magnetic resonance spectroscopy, GPC, differential scanning calorimetry (DSC), thermal gravimetric analysis, contact angle measurements, UV spectroscopy, mass spectroscopy, elemental analysis and high pressure liquid chromatography (HPLC).

The o-CPH monomer was polymerized by melt polycondensation for 60 minutes at temperatures ranging from 100° C. to 300° C. Analysis of the resulting polymers by GPC indicated that the highest molecular weight, coupled with the lowest polydispersity index occurred at 260° C.

The poly(o-CPH) was generally soluble in methylene chloride and chloroform, while the poly(p-CPH) was not. The poly(o-CPH) was slightly soluble in tetrahydrofuran, acetone and ethyl acetate.

Disks of poly(o-CPH), poly(p-CPH) and, as a reference, poly(lactic acid glycolic acid) were prepared and placed in 0.1 phosphate buffer solution at 37° C. for 4 weeks. The degradation media was replaced periodically. The degradation profile was linear up to three weeks time. In prior art polyanhydride systems, the aromatic groups are parasubstituted. This substitution pattern results in higher melt and glass transition temperatures and decreased solubility, thus ultimately making these parasubstituted polymers difficult to process.

Poly(o-CPH), unlike poly(p-CPH), has both a lower melting point (65° C. vs. 143° C.) and glass transition temperature (35° C. vs. 47° C.). It is also possible to solution cast poly(o-CPH) using low-boiling solvents whereas poly(p-CPH) is relatively insoluble in most organic and aqueous solvents. This structural modification gives a polymer whose hydrolysis products are chemically similar to aspirin. Aspirin is an anti-inflammatory agent derived from salicylic acid, which is one of the reagents used to synthesize the inventive polyanhydrides. Therefore, the degradation products of this polymer actually aid in patient recovery. Because of pliability and ease of processing, the aromatic polyanhydrides of the present invention have great potential as polymer scaffolds for wound healing.

Example 4

Preparation of 1,3-bis(o-Carboxyphenoxy)propane Dicarboxylic Acid 1,3-dibromopropane (14.7 mL, 0.145 mole) was added to a mixture of salicylic acid (40.0 g, 0.290 mole), distilled water (44 mL) and sodium hydroxide (23.2 g, 0.580 mole) using the method described in Example 1. After 4 hours, additional sodium hydroxide (5.79 g, 0.145 mole) was added to the reaction mixture. Reflux was continued for another 4 hours, after which the mixture was cooled, filtered and washed using the methods described in Example 1. The yield was 37.7%

Example 5

Preparation of Poly(1,3-bis(o-Carboxyphenoxy) propane)

The dicarboxylic acid of Example 4 was acetylated using the methods of Example 2. The acetylated dicarboxylic acid was then polymerized using the methods described in Example 3. The resulting polymer had a $M_w$ of 8,500 daltons and a polydispersity of 2.3.

Contact angle measurements on solvent-cast films demonstrated that the hexyl chain of the polymer of Example 3 increased the surface hydrophobicity relative to the shorter propyl chain of the polymer of Example 5. A comparison of thermal characteristics emphasized the effects of lengthening the alkyl chain. In particular, the polymer of Example 3 has a $T_g$ of 34° C. and a $T_d$ of 410° C., while the polymer of Example had a $T_g$ of 50° C. and a $T_d$ of 344° C. Thus, the hexyl chain decreased the glass transition temperature ($T_g$) relative to the propyl chain, reflecting the increased flexibility of the polymer chain. The opposite trend was observed for decomposition temperatures ($T_d$), with the longer alkyl chain increasing the $T_d$.

Optimum polycondensation conditions were determined for the polymer of Example 3. Optimum conditions were defined as those that yielded a crude polymer with the highest molecular weight and highest $T_g$. Higher reaction temperatures decreased the $M_w$ values (measured by GPC) with a concurrent increase in polydispersity. As expected for a condensation polymerization, longer reaction times yielded polymers with higher molecular weights. However, over longer reaction times, there appeared a subsequent decrease in $T_g$. Based on these results, the optimum conditions were defined as temperatures of 220° C. for 150 minutes under a vacuum.

Example 6

Preparation of 1,8-bis[o-(Benzylcarboxy)carboxy phenyl]octane Dicarboxylic Acid Ester The initial synthesis of poly(anhydride-ester) dicarboxylic acid monomers was attempted using the same methodology used for the poly(anhydride-ether) dicarboxylic monomers of Example 3. It was found, however, that the reactivity of the phenol was enhanced by benzylation of the carboxylic acid group. In addition, the solubility of benzyl salicylate in organic media increased the ability of the reaction to move forward.

Thus, benzyl salicylate (1.530 g, 6.720 mmole) and distilled tetrahydrofuran were combined under an inert atmosphere in a reaction flask. An ice-salt bath was placed under the reaction flask and the addition of 60% sodium hydride (0.4840 g, 12.10 mmole) followed. After one hour, sebacoyl chloride (0.7850 g, 3.280 mmole) was added drop-wise to the 0° C. reaction mixture. After minutes, the reaction mixture was vacuum filtered, the filtrate collected and the solvent removed to yield the free carboxylate as a white solid residue. Purification was performed using a chromatron with ethyl acetate/methylene chloride (20/80) as the solvent system. The yield was 43%.

Example 7

Polymerization of Poly(1,8-bis(o-dicarboxyphenyl) octane)

To remove the benzyl protecting groups, the 1,8-bis [(benzylcarboxy)carboxyphenyl]octane dicarboxylic acid ester of Example 6 (0.06000 g, 0.9620 mmole) was dissolved in methylene chloride in a reaction flask (60.00 mL). The catalyst Pd-C (10%, 1.200 g) was added to the reaction flask. After minutes, the reaction was complete. The reaction mixture was filtered and the solvent removed to yield the free dicarboxylic acid as a white solid residue which was recrystallized using petroleum ether and methylene chloride. The yield was 45%.

The dicarboxylic acid was acetylated using the methods described in Example 2 and the acetylated dicarboxylic acid was then polymerized using the methods described in Example 3. The resulting polymer had a $M_w$ of 3,000 daltons and a polydispersity of 1.40.

Subsequent polymerizations yielded polymers with $M_w$'s ranging from 2,000 to 5,000 daltons with corresponding polydispersities of approximately 1.40.

The poly(anhydride esters) of Example 7 were compression molded into circular discs and placed in phosphate buffered saline solution under acidic, neutral and basic conditions. Over the course of a three-week degradation study, the polymers in the acidic and neutral solutions showed no observable changes, whereas the polymer in the basic media showed significant morphological changes over time.

Example 8

Preparation of Poly[(1,8-bis(o-dicarboxyphenyl) octane)-(1,6-bis(p-carboxyphenoxy)hexane] Copolymers The 1,8-bis(o-dicarboxyphenyl) octane of Example 2 was copolymerized with 1,6-bis(p-carboxyphenoxy) hexane using the methods described in Example 3. In an in vivo mouse study, each mouse was implanted with 2 polymers, the copolymer of Example 8 and poly(1,6-bis(p-carboxyphenoxy)hexane). Each polymer was compression molded for 1 to 5 minutes at 1 to 20 K psi depending on the thickness of polymer needed. The polymer was placed under the palatal gingival mucosa adjacent to the first maxillary molars.

What is claimed is:

1. A composition comprising a polyanhydride which degrades to a biologically active alpha-hydroxy acid, said polyanhydride comprising a repeating unit having the structure of Formula (III):

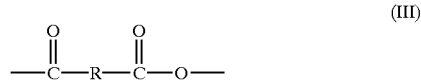

wherein R is of the formula —$(CHZ_1)_x$— wherein x is from 1 to 20 and $Z_1$ is OH or H and at least one $Z_1$ is OH.

2. A method of delivering an alpha-hydroxy acid to a host comprising administering to a host a composition of claim 1 wherein the polyanhydride comprises Formula (III).

3. A method of delivering an alpha-hydroxy acid to a host comprising administering to a host a composition comprising a polyanhydride which degrades to a biologically active alpha-hydroxy acid, the polyanhydride comprising a repeating unit having the structure of Formula (III):

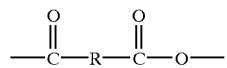
(III)

wherein R is of the formula —$(CHZ_1)_x$— wherein x is from 1 to 20 and $Z_1$ is OH or H and wherein the composition is administered topically to promote smoother, clearer skin with less wrinkles.

4. The composition in accordance with claim 1, wherein the alpha-hydroxy acid is malic acid.

5. A polyanhydride which degrades into a biologically active alpha-hydroxy acid which is citric acid or malic acid.

6. A method of delivering an alpha-hydroxy acid to a host comprising administering to the host the polyanhydride of claim 5.

7. The method in accordance with claim 3, wherein the alpha-hydroxy acid is malic acid or citric acid.

8. The method in accordance with claim 3, wherein x is 2 and at least one $Z_1$ is —OH.

* * * * *